US012376824B2

United States Patent
Robinson et al.

(10) Patent No.: US 12,376,824 B2
(45) Date of Patent: Aug. 5, 2025

(54) METHODS, SYSTEMS, AND COMPUTER READABLE MEDIA FOR UTILIZING A THERAPEUTIC ULTRASOUND DEVICE TO PERFORM MITRAL VALVE DECALCIFICATION

(71) Applicant: University of Virginia Patent Foundation, Charlottesville, VA (US)

(72) Inventors: Austin A. Robinson, Charlottesville, VA (US); Christopher M. Kramer, Charlottesville, VA (US); John A. Hossack, Charlottesville, VA (US); Patricia Fiorella Rodriguez Lozano, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 127 days.

(21) Appl. No.: 17/770,431

(22) PCT Filed: Oct. 21, 2020

(86) PCT No.: PCT/US2020/056680
§ 371 (c)(1),
(2) Date: Apr. 20, 2022

(87) PCT Pub. No.: WO2021/081105
PCT Pub. Date: Apr. 29, 2021

(65) Prior Publication Data
US 2022/0409169 A1    Dec. 29, 2022

Related U.S. Application Data

(60) Provisional application No. 62/923,776, filed on Oct. 21, 2019.

(51) Int. Cl.
*A61B 8/08*   (2006.01)
*A61B 8/00*   (2006.01)
(Continued)

(52) U.S. Cl.
CPC .......... *A61B 8/0883* (2013.01); *A61B 8/488* (2013.01); *A61B 34/10* (2016.02); *A61B 2017/00044* (2013.01)

(58) Field of Classification Search
CPC ....... A61B 8/0883; A61B 8/488; A61B 34/10; A61B 2017/00044; A61B 17/22004;
(Continued)

(56) References Cited

U.S. PATENT DOCUMENTS

| 7,402,136 B2 | 7/2008 | Hossack et al. |
| 7,699,776 B2 | 4/2010 | Walker |

(Continued)

FOREIGN PATENT DOCUMENTS

| CA | 2981219 A1 | 10/2016 |
| EP | 3236467 A1 | 10/2017 |

(Continued)

OTHER PUBLICATIONS

Timek et al. 2001 Ann. Thorac. Surg. 72:966â74 (Year: 2001).*
(Continued)

*Primary Examiner* — Keith M Raymond
*Assistant Examiner* — Patrick M Mehl
(74) *Attorney, Agent, or Firm* — Jenkins, Taylor & Hunt, P.A.

(57) ABSTRACT

Methods, systems, and computer readable media for utilizing a therapeutic ultrasound device to perform mitral valve decalcification are disclosed. One method includes acquiring, via an ultrasound imaging component, imaging data of a mitral valve in real-time, defining a therapeutic region of interest corresponding to the mitral valve, and utilizing, by a system controller engine, imaging data from the ultrasound imaging component to determine an interval period of minimal mitral annular movement. The method further includes defining a sequence of therapeutic targets within (Continued)

the region of interest of the mitral valve, utilizing the imaging data acquired in real-time by the ultrasound imaging component to provide a therapeutic ultrasound transducer array with a location and depth of an intra-annular focal zone within the mitral valve, and emitting a high intensity focused ultrasound (HIFU) pulse wave from the therapeutic ultrasound transducer array to each of the therapeutic targets of the mitral valve during the determined interval period and in accordance with the defined sequence.

19 Claims, 5 Drawing Sheets

(51) Int. Cl.
  *A61B 17/00* (2006.01)
  *A61B 34/10* (2016.01)

(58) Field of Classification Search
  CPC .......... A61B 2017/00106; A61B 2017/22098; A61B 2090/378; A61N 2007/0039; A61N 2007/0065; A61N 7/00
  See application file for complete search history.

(56) References Cited

U.S. PATENT DOCUMENTS

| | | |
|---|---|---|
| 7,750,537 B2 | 7/2010 | Hossack et al. |
| 8,057,392 B2 | 11/2011 | Hossack |
| 8,093,782 B1 | 1/2012 | Hossack |
| 8,440,167 B2 | 5/2013 | Beller |
| 8,622,911 B2 | 1/2014 | Hossack et al. |
| 8,700,127 B2 | 4/2014 | Salerno et al. |
| 9,002,080 B2 | 4/2015 | Mauldin, Jr. et al. |
| 9,144,694 B2 | 9/2015 | Cain |
| 9,237,898 B2 | 1/2016 | Hossack et al. |
| 9,244,160 B2 | 1/2016 | Blalock et al. |
| 9,275,630 B2 | 3/2016 | Blalock et al. |
| 9,445,780 B2 | 9/2016 | Hossack et al. |
| 9,526,922 B2 | 12/2016 | Hossack et al. |
| 9,642,634 B2 | 5/2017 | Cain et al. |
| 9,814,476 B2 | 11/2017 | Adams et al. |
| 9,895,158 B2 | 2/2018 | Dixon et al. |
| 9,910,118 B2 | 3/2018 | Feng |
| 9,924,923 B2 | 3/2018 | Mauldin, Jr. et al. |
| 9,943,708 B2 | 4/2018 | Roberts et al. |
| 9,949,722 B2 | 4/2018 | Mauldin, Jr. et al. |
| 9,953,439 B2 | 4/2018 | Salerno et al. |
| 9,989,497 B2 | 6/2018 | Walker et al. |
| 10,368,834 B2 | 8/2019 | Mauldin, Jr. et al. |
| 10,401,327 B2 | 9/2019 | Hu et al. |
| 11,617,901 B2 | 4/2023 | Brenin et al. |
| 2007/0016022 A1 | 1/2007 | Blalock et al. |
| 2010/0168578 A1 | 7/2010 | Garson, Jr. et al. |
| 2010/0268086 A1 | 10/2010 | Walker |
| 2012/0029356 A1 | 2/2012 | Hossack |
| 2013/0190623 A1 | 7/2013 | Bertolina et al. |
| 2015/0011884 A1 | 1/2015 | Walker et al. |
| 2015/0025387 A1 | 1/2015 | Hossack |
| 2016/0206867 A1 | 7/2016 | Hossack et al. |
| 2017/0000458 A1 | 1/2017 | Blalock et al. |
| 2017/0196534 A1 | 7/2017 | Hossack et al. |
| 2017/0281130 A1 | 10/2017 | Dixon et al. |
| 2018/0035979 A1 | 2/2018 | Herbst et al. |
| 2018/0064412 A1* | 3/2018 | Messas ............... A61B 8/06 |
| 2018/0099059 A1 | 4/2018 | Hossack et al. |
| 2018/0214130 A1 | 8/2018 | Hossack et al. |
| 2019/0083817 A1 | 3/2019 | Okusa et al. |
| 2019/0279361 A1 | 9/2019 | Meyer et al. |

FOREIGN PATENT DOCUMENTS

| | | | |
|---|---|---|---|
| WO | WO 03/075769 A1 | 9/2003 | |
| WO | WO 2004/064619 A2 | 8/2004 | |
| WO | WO 2004/064620 A2 | 8/2004 | |
| WO | WO 2004/065978 A2 | 8/2004 | |
| WO | WO-2005000097 A2 * | 1/2005 | ............... A61B 8/12 |
| WO | WO 2006/042067 A2 | 4/2006 | |
| WO | WO 2007/140331 A3 | 12/2007 | |
| WO | WO 2008/154632 A2 | 12/2008 | |
| WO | WO 2009/055720 A1 | 4/2009 | |
| WO | WO 2010/021709 A1 | 2/2010 | |
| WO | WO 2010/062557 A2 | 6/2010 | |
| WO | WO 2011/011539 A1 | 1/2011 | |
| WO | WO 2012/148985 A1 | 11/2012 | |
| WO | WO 2013/188625 A1 | 12/2013 | |
| WO | WO 2016/040008 A1 | 3/2016 | |
| WO | WO 2016/094434 A1 | 6/2016 | |
| WO | WO 2017/019873 A1 | 2/2017 | |
| WO | WO 2017/192754 A1 | 11/2017 | |
| WO | WO 2019/199940 A1 | 10/2019 | |
| WO | WO 2021/081105 A1 | 4/2021 | |

OTHER PUBLICATIONS

International Preliminary Report on Patentability Corresponding to International Patent Application No. PCT/US 2020/056680 dated May 5, 2020.

International Search Report and Written Opinion of the International Searching Authority Corresponding to International Patent Application No. PCT/US 2020/056680 dated Jan. 22, 2021.

Ali, Z.A., et al., "Optical Coherence Tomography Characterization of Coronary Lithoplasty for Treatment of Calcified Lesions," First description. JACC: Cardiovascular Imaging, vol. 10, No. 8, 2017, pp. 897-906.

Bailey, M.R., et al., "Cavitation Detection During Shock-Wave Lithotripsy," Ultrasound in Med & Biol., vol. 31, No. 9, 2005, pp. 1245-1256.

Baumgartner, F.J., et al., "Ultrasonic Debridement of Mitral Calcification," J Card Surg., No. 12, 1997, pp. 240-242.

Bond, A.E., et al., "Safety and Efficacy of Focused Ultrasound Thalamotomy for Patients with Medication-Refractory, Tremor-Dominant Parkinson Disease: A Randomized Clinical Trial," JAMA Neurology. 2017; 74:1412-8.

Brown, A.H., et al., "Ultrasonic decalcification of calcified cardiac valves and annuli," British Medical Journal, vol. 3, 1972, pp. 274-277.

Burneikaite, G., et al., "Cardiac Shock-Wave Therapy in the Treatment of Coronary Artery dlsease: Systematic review and Meta-Analysis," Cardiovascular Ultrasound. 2017; 15:11, p. 13.

Carpentier, A.F., et al., "Extensive Calcification of the Mitral Valve Anulus: Pathology and Surgical Management," The Journal of Thoracic and Cardiovascular Surgery, vol. 111, No. 4,1996, pp. 718-730.

Chaussy, C., et al., "Extracorporeally Induced Destruction of Kidney Stones by Shock Waves," The Lancet, vol. 316, 1980, pp. 1265-1268.

"Edwards Acquires Harpoon Medical," Heart Valve Technology, accessed at https://www.dicardiology.com/content/edwards-acquires-harpoon-medical, dated Dec. 7, 2017, p. 7.

Eleid, M, F., et al., "Early Outcomes of Percutaneous Transvenous Transseptal Transcatheter Valve Implantation in Failed Bioprosthetic Mitral Valves, Ring Annuloplasty, and Severe Mitral Annular Calcification," JACC: Cardiovascular Interventions, vol. 10 no. 19, 2017, pp. 1932-1942.

Eleid M. F., et al., "Severe Mitral Annular Calcification: Multimodality Imaging for Therapeutic Strategies and Interventions," JACC: Cardiovascular Imaging, vol. 9, No. 11, 2016, pp. 1318-1337.

Evan, A.P., et al., "Renal Injury During Shock Wave Lithotripsy is Significantly Reduced by Slowing The Rate Of Shock Wave Delivery," BJU International, vol. 100, 2007, pp. 624-628.

Feindel, C.M., "Getting Beyond the "bar of death" in Complex Rheumatic Mitral Valve Surgery," The Journal of Thoracic and Cardiovascular Surgery, vol. 149, No. 5, 2015, pp. 1455-1456.

Feindel, C.M., et al. "Mitral Valve Surgery in Patients with Extensive Calcification of The Mitral Annulus," The Journal of Thoracic and Cardiovascular Surgery, vol. 126, No. 3, 2003, pp. 777-781.

(56) References Cited

OTHER PUBLICATIONS

Gatlin, A., "Abbott Tops Bearish Odds In 'Landmark' Study of Heart Device," Technology accessed at https://www.investors.com/news/technology/abbott-boston-cardiovascular-device-studies/ dated Sep. 24, 2018, p. 4.
Gordis, L., "The Virtual Disappearance of Rheumatic Fever in The United States: Lessons in The Rise And Fall of Disease," T. Duckett Jones Memorial Lecture, Circulation, vol. 72, No. 6, Dec. 1985, pp. 1155-1162.
Guerrero, M., et al., "1-year Outcomes of Transcatheter Mitral Valve Replacement In Patients With Severe Mitral Annular Calcification," Journal of American College of Cardiology, vol. 71, No. 17, 2018, pp. 1841-1853.
Guerrero, M., et al., "Transcatheter Mitral Valve Replacement in Native Mitral Valve Disease With Severe Mitral Annular Calcification: Results From The First Multicenter Global Registry," JACC: Cardiovascular Interventions, vol. 9, No. 13, 2016, pp. 1361-1371.
Horstkotte, D., et al., "Pathomorphological Aspects, Aetiology and Natural History of Acquired Mitral Valve Stenosis," European Herat Journal, vol. 12, 1991, pp. 55-60.
Kuhn, C., et al., "Impact of Extracorporeal Shock Waves on The Human Skin With Cellulite: A Case Study of an Unique Instance," Clinical Interventions in Aging, vol. 3, 2008, pp. 201-210.
Labovitz, A. J., et al., "Frequency of Mitral Valve Dysfunction from Mitral Anular Calcium as Detected By Doppler Echocardiography," Am J Cardiol, vol. 55, 1985, pp. 133-137.
Lad, V.S., et al., "SUrgical Techniques for the Management of the 'Hostile Mitral Annulus," Heart, Lung and Circulation, vol. 23, 2014, pp. 217-223.
Loew, M., et al., "Initial Experiences with Extracorporeal Shockwave Lithotripsy (ESWL) In Treatment of Tendinosis Calcarea Of the Shoulder," Z Orthop Ihre Grenzgeb., vol. 131, 1993, pp. 470-473.
Loew, M., et al., "Shock-wave Therapy is Effective for Chronic Calcifying Tendinitis of the Shoulder," The Journal of Bone & Joint Surgery (Br), vol. 81-B, No. 5, Sep. 1999, pp. 863-867.
Lung, B., et al., "A Prospective Survey of Patients with Valvular Heart Disease in Europe: The Euro Heart Survey on Valvular Heart Disease," European Heart Journal, vol. 24, 2003, pp. 1231-1243.
Messenger, J.C., "Trends in United States TAVR Practice," Cardiac Interventions Today, March/Apr. 2018, vol. 12, No. 2, pp. 46-50.
Nkomo, V.T., et al., "Burden of Valvular Heart Diseases: A Population-based Study," The Lancet, vol. 368, Sep. 16, 2006, pp. 1005-1011.
Okada, Y., "Surgical Management of Mitral Annular Calcification," General Thoracic And Cardiovascular Surgery, vol. 61, 2013, pp. 619-625.
Papadopoulos, N., et al., "Midterm Survival After Decalcification of the Mitral Annulus," Ann Thorac Surg, vol. 87, 2009, pp. 1143-1147.
Pasca, I., et al., "Survival in Patients with Degenerative Mitral Stenosis: Results from a Large Retrospective Cohort Study," Journal of the American Society of Echocardiography, vol. 29, 2016, pp. 461-469.
Ramzy, D., et al. "Transcatheter Mitral Valve Replacement for Severe Mitral Annular Calcification: Is it Ready for Prime Time? ," Journal of the American Cardiology, vol. 71, No. 17, 2018, pp. 1854-1856.
Rosenschein, U., et al., "Experimental Ultrasonic Angioplasty: Disruption Of Atherosclerotic Plaques and Thrombi in Vitro and Arterial Recanalization in Vivo," J Am Coll Cardiol., vol. 15, 1990, pp. 711-717.
Rosenschein, U., et al., "Shock-wave Thrombus Ablation, A New Method for Noninvasive Mechanical Thrombolysis," The American Journal of Cardiology, vol. 70, Nov. 15, 1992, pp. 1358-1361.
Rosenschein, U., et al., "Ultrasound Imaging-guided Noninvasive Ultrasound Thrombolysis: Preclinical Results," Circulation, vol. 102, 2000, pp. 238-245.
Russell, H.M., et al., "Original Investigation Open Atrial Transcatheter Mitral Valve Replacement In Patients With Mitral Annular Calcification," The Journal of Thoracic and Cardiovascular Surgery, vol. 157, No. 3, 2018, pp. 907-916.
Smith, R.L., "Surgical Implantation of TRAnscatheter valve in Native Mitral Annular Calcification (SITRAL) Study (Sitral)," NCT02830204, Baylor Research Institute, accessed at https://clinicaltrials.gov/ct2/show/NCT02830204 dated Jan. 16, 2024, p. 13.
Stone, G.W., et al., "Transcatheter Mitral-valve Repair in Patients with Heart Failure," The New England Journal of Medicine, vol. 379, No. 24, Dec. 13, 2018, pp. 2307-2318.
Sud, K., et al. "Degenerative Mitral Stenosis: Unmet Need for Percutaneous Interventions," Circulation, vol. 133, 2016, pp. 1594-1604, Doi: 10.1161/CIRCULATIONHA. 115.020185.
Vainer, J., et al., "Cardiac Shockwave Therapy in Patients with Chronic Refractory Angina Pectoris," Netherlands Heart Journal, vol. 24, 2016, pp. 343-349.
Villemain, O., et al., "Pulsed Cavitational Ultrasound Softening," JACC Basic Translational Science, vol. 8, 2017, pp. 372-383.
Yang, et al., "Randomized and Double-blind Controlled Clinical Trial of Extracorporeal Cardiac Shock Wave Therapy for Coronary Heart Disease," Heart Vessels, vol. 2013, pp. 284-291.

\* cited by examiner

METHODS, SYSTEMS, AND COMPUTER READABLE MEDIA FOR UTILIZING A THERAPEUTIC ULTRASOUND DEVICE TO PERFORM MITRAL VALVE DECALCIFICATION

RELATED APPLICATIONS

The presently disclosed subject matter claims the benefit of U.S. Provisional Patent Application Ser. No. 62/923,776 filed Oct. 21, 2019, the disclosure of which is incorporated herein by reference in its entirety.

TECHNICAL FIELD

The presently disclosed subject matter relates generally to methods and devices for therapeutic treatment for degenerative mitral stenosis and mitral annual calcification. More particularly, in some embodiments, the present subject matter described herein relates to methods, systems, and computer readable media for utilizing a therapeutic ultrasound device to perform mitral valve decalcification.

BACKGROUND

Degenerative mitral stenosis (DMS), which can be caused by calcification of the mitral valve structure within the heart, is a life-limiting condition that is not easily treated with contemporary medical and surgical approaches. Percutaneous techniques attempting to treat DMS also have demonstrated significant problems. In many instances, mitral stenosis (MS) is typically associated with rheumatic heart disease, which is its most prevalent global cause. Some surveys estimated the proportion of mitral stenosis that is due to DMS is at approximately 12.5%, with rapidly increasing prevalence by decade. Namely, from approximately 10% in the seventh decade to 60% of all mitral stenosis in those greater than 80 years old. However, the combination of increasing life expectancy with reductions in rheumatic heart disease in developed nations has certainly led to increases in the number of cases of MS attributable to degenerative disease, specifically mitral annular calcification (MAC). MAC typically involves the posterior annulus, without hemodynamic significance. However, calcification process sometimes extends to the mitral leaflets, reducing mitral leaflet mobility and restricting mitral annular expansion in diastole, resulting in inflow restriction and consequent calcific MS. Many studies, including invasive confirmation of echocardiographic findings, suggest that approximately 8% of patients with MAC have some degree of hemodynamically significant MS. Severe DMS also carries an unfavorable prognosis, i.e., a one-year survival rate estimated at approximately 60% in a recent study.

There are several problems with the current therapeutic strategies for DMS. Medical therapy, consisting of diuretics and heart rate control, provides symptomatic benefit but fails to modify disease progression. Surgery for MAC poses several technical challenges. In valve replacement, the presence of annular calcium itself is a risk factor for subsequent re-operation. The process of annular calcium debridement is difficult to perform and risks serious complications, including aortic valve (AV) groove separation, left ventricular rupture, and injury to the left circumflex artery. Such operative difficulties involving MAC have earned it the appellation, "bar of death," in the surgical literature.

Likewise, percutaneous mitral valve replacement strategies, either with prosthesis designed for the aortic valve or dedicated mitral devices have encountered significant problems, including left ventricular outflow tract (LVOT) obstruction, paravalvular leak, and inadequate prosthesis anchoring. Results from registries are sobering. Some registries indicate a 20% rate of procedural complications in outcomes of several types of balloon-expandable valves for MAC-related mitral valve disease. These complications include LVOT obstruction, device embolization, and perforation. Notably, the mortality in these patients (11 of 13) approached 85% and the updated, 1-year outcomes data were even worse, with a 30-day mortality of 25% and 1-year mortality of 53.7%.

Another registry of mitral valve replacement delivered via a trans-septal approach underscored the difficulty of anchoring transcatheter valves in MAC. Specifically, 71% of patients experienced a significant complication such as cardiac tamponade, embolization, lethal LVOT obstruction, severe regurgitation, or major bleed. Aggregated with valves in mitral annuloplasty rings, valves in MAC had a significantly lower survival rate free of death or cardiovascular surgery when compared with valves in failed bioprosthetic valves.

Consequently, the aforementioned difficulties have created a therapeutic vacuum for patients with degenerative mitral stenosis. Namely, the vast majority of patients with mitral valve disease due to severe MAC are oftentimes simply deemed inoperable and are left untreated, which leaves a significant unmet need for treatment of this patient population.

SUMMARY

Methods, systems, and computer readable media for utilizing a therapeutic ultrasound device to perform mitral valve decalcification are disclosed. One method includes acquiring, via an ultrasound imaging component, imaging data of a mitral valve in real-time, defining a therapeutic region of interest corresponding to the mitral valve, and utilizing, by a system controller engine, imaging data from the ultrasound imaging component to determine an interval period of minimal mitral annular movement. The method further includes defining a sequence of therapeutic targets within the region of interest of the mitral valve, utilizing the imaging data acquired in real-time by the ultrasound imaging component to provide a therapeutic ultrasound transducer array with a location and depth of an intra-annular focal zone within the mitral valve, and emitting a high intensity focused ultrasound (HIFU) pulse wave from the therapeutic ultrasound transducer array to each of the therapeutic targets of the mitral valve during the determined interval period and in accordance with the defined sequence.

According to another aspect of the subject matter described herein, a method wherein the imaging component and the therapeutic ultrasound transducer array are synchronized by the system controller engine in such a manner that the ultrasound imaging component and the therapeutic ultrasound transducer array are prevented from operating simultaneously.

According to another aspect of the subject matter described herein, a method wherein the system controller engine is configured to determine cardiac phases associated with at least an annular movement exhibited by the mitral valve and to subsequently select a timing of a therapeutic ultrasound application based on the determined cardiac phases.

According to another aspect of the subject matter described herein, a method wherein the therapeutic ultrasound transducer array is configured to be located externally to a patient body.

According to another aspect of the subject matter described herein, a method wherein the ultrasound imaging component is configured to generate two-dimensional echocardiographic views of the mitral valve.

According to another aspect of the subject matter described herein, a method wherein the ultrasound imaging component is configured to determine a foci of calcification within an annular sheath of the mitral valve.

According to another aspect of the subject matter described herein, a method further comprising utilizing the ultrasound imaging component to identify regions of intra-annular and extra-annular calcification in the mitral valve.

According to another aspect of the subject matter described herein, a method wherein defining a sequence of therapeutic targets within the region of interest of the mitral valve further includes selecting intra-annular calcium foci as the therapeutic targets and avoiding extra-annular calcium.

According to another aspect of the subject matter described herein, a method further comprising utilizing the ultrasound imaging component to confirm the presence and location of cavitation in the mitral valve, maintain annular sheath integrity in the mitral valve, and monitor for potential calcific emboli.

In another embodiment, a system for utilizing a therapeutic ultrasound device to perform mitral valve decalcification is disclosed. The system includes a therapeutic ultrasound transducer array comprising a plurality of therapeutic transducer elements configured to generate a high-intensity focused ultrasound (HIFU) pulse wave that is directed to a mitral valve of a target patient. The system further includes an ultrasound imaging component configured for capturing images corresponding to the mitral valve and for providing real-time steering guidance for the therapeutic ultrasound transducer array and a system controller engine for coordinating an alternating operation of the ultrasound imaging component and the therapeutic ultrasound transducer array with respect to annular movement exhibited by the mitral valve.

According to another aspect of the subject matter described herein, a system wherein the imaging component and the therapeutic ultrasound transducer array are synchronized by the system controller engine in such a manner that the ultrasound imaging component and the therapeutic ultrasound transducer array are prevented from operating simultaneously.

According to another aspect of the subject matter described herein, a system wherein the system controller engine is further configured to identify an interval period of minimal annular movement exhibited by the mitral valve.

According to another aspect of the subject matter described herein, a system wherein the system controller engine is configured to determine cardiac phases associated with at least the annular movement exhibited by the mitral valve and to subsequently select a timing of therapeutic ultrasound application based on the determined cardiac phases.

According to another aspect of the subject matter described herein, a system wherein the therapeutic ultrasound transducer array is configured to be located external to the body of the target patient.

According to another aspect of the subject matter described herein, a system wherein the ultrasound imaging component is configured to generate two-dimensional echocardiographic views of the mitral valve.

According to another aspect of the subject matter described herein, a system wherein the ultrasound imaging component is configured to determine a foci of calcification within the mitral valve.

The subject matter described herein may be implemented in hardware, software, firmware, or any combination thereof. As such, the terms "function", "engine" or "module" as used herein may refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

Accordingly, it is an object of the presently disclosed subject matter to provide methods, systems, and computer readable media for utilizing a therapeutic ultrasound device to perform mitral valve decalcification. An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

The subject matter described herein will now be explained with reference to the accompanying drawing of which.

DETAILED DESCRIPTION

The presently disclosed subject matter will now be described more fully. The presently disclosed subject matter can be embodied in different forms and should not be construed as limited to the embodiments set forth herein below. Rather, these embodiments are provided so that this disclosure will be thorough and complete, and will fully convey the scope of the embodiments to those skilled in the art.

The disclosed subject matter presents new methods of therapeutic ultrasound (TU) that can selectively target the mitral valve and can be delivered with minimally-invasive approaches that are conducted external to the patient body.

Notably, the disclosed subject matter includes a therapeutic ultrasound system that comprises a dual function imaging and cavitation ultrasound-based device and a related method for mitral valve decalcification. For example, the disclosed subject matter provides, among other things, a system, method, and computer readable medium for a multi-modality assessment and treatment of mitral valve disease and pulse wave therapy for the treatment of MAC-related mitral stenosis. One aspect of an embodiment of the disclosed TU system provides, among other things, a dual function (i.e., imaging and therapy) ultrasound transducer device that is synchronized so as to effect real-time image guidance before, during, and after the application of focal high intensity ultrasound pulse waves for the purpose of heart valve decalcification.

Figure 1:
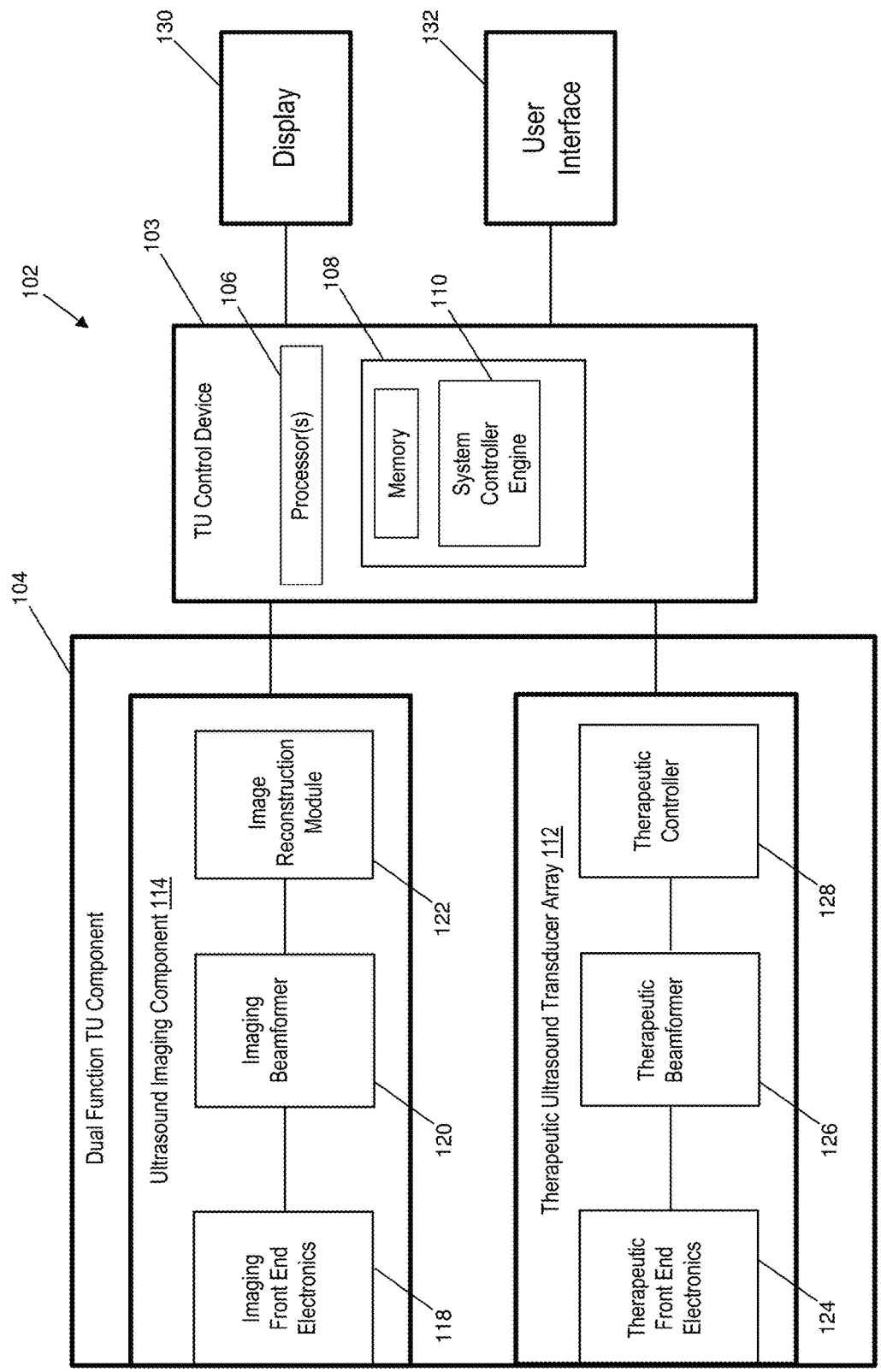
FIG. 1 is a block diagram of an exemplary therapeutic ultrasound system according to an embodiment of the subject matter described herein.
Figure 2:
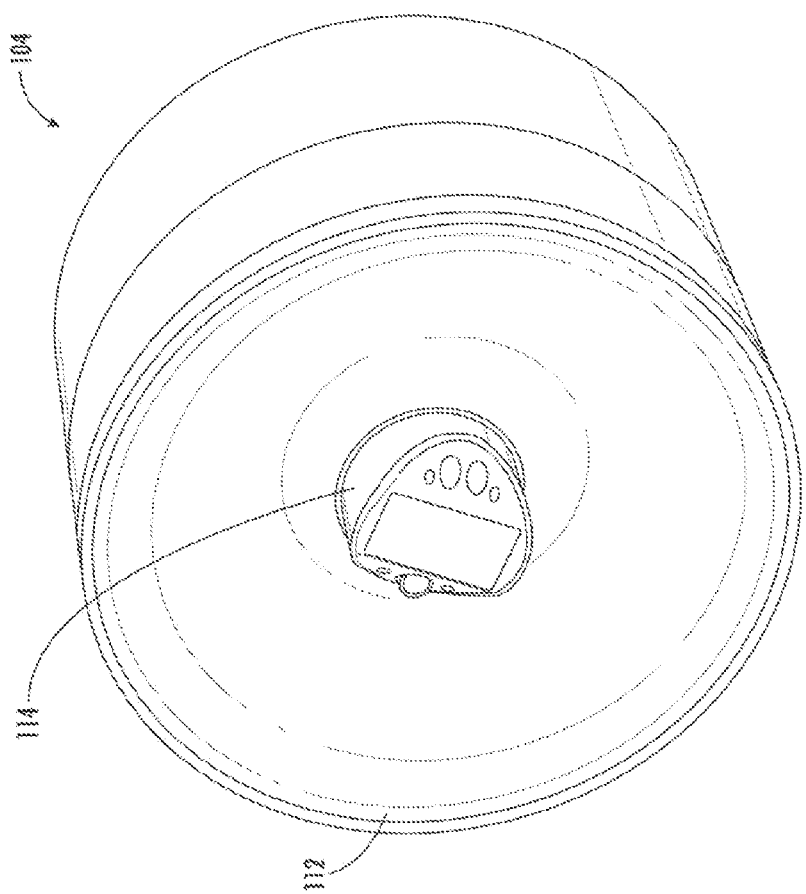
FIG. 2 is a schematic diagram of an exemplary dual function therapeutic component device according to an embodiment of the subject matter described herein.

FIG. 1 illustrates a block diagram of an exemplary therapeutic ultrasound system 102 according to an embodiment of the subject matter described herein. As shown in FIG. 1, therapeutic ultrasound system 102 includes a dual function TU component 104, a therapeutic ultrasound control device 103, a display 130 (e.g., a computer monitor or other screen display), and a user interface 132 (e.g., a keyboard, mouse, etc.). As shown in FIG. 1, TU control device 103 is communicatively connected to dual function TU component 104, user interface 132, and display 130. Dual function TU component 104 comprises a therapeutic ultrasound transducer array 112 and an ultrasound imaging component 114. An example of the dual function TU component 104 comprising therapeutic ultrasound transducer array 112 and ultrasound imaging component 114 is depicted in FIG. 2 and described in additional detail below.

In some embodiments, ultrasound imaging component 114 may comprise at least one imaging transducer element. As shown in FIG. 1, ultrasound imaging component 114 includes imaging front-end electronics 118, and imaging beamformer 120, and image reconstruction module 122. Imaging front end electronics 118 may include a plurality of electronics including analog circuitry, amplifiers, sensitive pre-amplifiers, protection switches used to provide component 104 to transmit and receive imaging related signals. Imaging front end electronics 118 further includes electrical channels that enable ultrasound imaging component 114 to generate a high power transmission and be adapted for low signal reception. Imaging beamformer 120 may comprise both a receiving and a transmit beamformer and is configured to control the sequencing of all of the electrical channels in ultrasound imaging component 114. Imaging beamformer 120 may also be adapted to generate the B-mode transmit signals and receive pulse-echo signals via front end electronics 118. Image reconstruction module 122 is configured for reconstructing the imaging data (e.g. radial data to cartesian data conversion/reconstruction) acquired by ultrasound imaging component 114. Reconstructed image data can then be provided to a system controller engine 110 hosted by TU control device 103 for processing described herein.

FIG. 1 further illustrates a therapeutic ultrasound transducer array 112 that includes imaging front-end electronics 124, a therapeutic beamformer 126, and therapeutic controller 128. In some embodiments, therapeutic front end electronics 124 is configured to emit a high powered transmission (e.g., pulse wave) and may include a plurality of necessary electronics including analog circuitry and amplifiers, and the like. Therapeutic front end electronics 124 can assist with the transmission of high intensity focused ultrasound (HIFU) pulse waves generated by therapeutic beamformer 126. In other embodiments, therapeutic ultrasound transducer array 112 can also further include front end electronics comprising sensitive pre-amplifiers and protection switches adapted to receive low powered signals. In such embodiments, therapeutic beamformer 126 can be configured to operate in a receiving mode in addition to the transmission mode. Similarly, therapeutic ultrasound transducer array 112 may include a therapeutic controller 128 that is responsible for defining the sequence foci (described below) as applied throughout a region of interest (ROI) in the mitral valve. In some embodiments, the functionality of therapeutic controller 128 may be included in a system controller engine 110 that is hosted in TU control device 103.

In FIG. 1, TU control device 103 includes at least one processor 106, memory 108, and a system controller engine 110. In some embodiments, processor 106 may comprise a central processing unit (e.g., a single core or multiple processing cores), a microprocessor, a microcontroller, a network processor, an application-specific integrated circuit (ASIC), or the like. Likewise, memory 108 may comprise random access memory (RAM), flash memory, a magnetic disk storage drive, and the like. In some embodiments, memory 108 can store a system controller engine 110 that includes software processes and/or an algorithm for managing the therapeutic ultrasound treatment conducted by TU system 102. In alternative embodiments, system controller engine 110 may comprise a hardware component or circuitry device (e.g., an application specific integrated circuit or a field programmable gate array device) that is configured to conduct and manage the disclosed therapeutic ultrasound treatment.

In some embodiments, dual function TU component 104 can include any device or component that is configured to deliver a high intensity, relatively low frequency, ultrasound. For example, dual function TU component 104 can be a paired cardiology imaging transducer system that incorporates a 128-element or a 256-element high intensity focused ultrasound (HIFU) transducer array. Notably, dual function TU component 104 is configured such that the HIFU plane corresponding to the transducer array 112 and the image plane corresponding to the ultrasound imaging component 104 are coincident. In alternative embodiments, other pairings of an ultrasound imaging component and a therapeutic ultrasound transducer array can be implemented.

In some embodiments, ultrasound imaging component 114 can be used to provide real-time imaging guidance that is necessary to perform clinical procedures. For example, ultrasound imaging component 114 may include a 64 channel B-mode cardiology transducer element. It is understood that alternative designs and/or devices are feasible, such as a two-dimensional array that is capable of real-time three-dimensional imaging. Ultrasound imaging component 114 can also be configured to detect the presence of calcification that is present in a mitral valve of a patient target. Likewise, ultrasound imaging component 114 can also be configured to detect the reduction of calcification due to the decalcifying operation conducted by TU system 102. For example, highly organized calcification in a mitral valve (e.g., mitral annulus) may be detected by ultrasound imaging component 114 by being a source of a strong coherent echo that is readily recognized as a calcified region. It is understood that more advanced methods of mitral calcification detection can also be employed by ultrasound imaging component 114. For example, ultrasound imaging component 114 can be configured for quantitative ultrasound (QUS) approaches, conducting backscatter brightness tracking, or executing methods that detect a higher modulus of calcification, such as elasticity imaging.

In some embodiments, therapeutic ultrasound transducer array 112 comprises a plurality of therapeutic transducer elements configured to generate a HIFU pulse wave that is emitted in a manner that is external to the patient body and heart. The generated pulse wave can be directed toward a mitral valve of the target patient utilizing guidance information provided by the ultrasound imaging component 114. In some embodiments, specifications of the therapeutic transducer elements include a 1.11 megahertz (MHz) operating frequency and a 150 mm radius. Notably, operating frequencies ranging from about 0.5 Mhz to about 2.0 Mhz are feasible and within the scope of the disclosed subject matter. In some embodiments, therapeutic ultrasound system 102 includes 128 (or 256) therapeutic transducer elements that are arranged in an Archimedean spiral. Guidance of therapeutic ultrasound transducer array 112 can be achieved using B-mode ultrasound guidance provided by images generated by ultrasound imaging component 114. In some embodiments, an imaging transducer element can be placed in the central aperture of a therapeutic transducer element. In some embodiments, power to the therapeutic transducer elements of transducer array 112 can be adjusted to achieve the peak negative pressure of −20 MPa or greater.

In some embodiments, system controller engine 110 is responsible for coordinating and synchronizing the operation of therapeutic ultrasound transducer array 112 and ultrasound imaging component 114. In particular, the imaging operations of ultrasound imaging component 114 and the decalcification operations of therapeutic ultrasound transducer array 112 are time synchronized so that the two modes/components are never utilized in the same instance (i.e., not operating in a simultaneous manner). In some embodiments, system controller engine 110 is configured with a gated-imaging synchronization algorithm that enables transducer array 112 and ultrasound imaging component 114 to operate in an alternating manner in order to achieve this goal.

As indicated above, therapeutic ultrasound system 102 can be configured to provide, among other things, a dual function TU component that is synchronized so as to effect real-time image guidance before, during, and after the application of focal high intensity ultrasound pulse waves for the purpose of heart valve decalcification. For example, ultrasound imaging component 114 can be configured to provide real-time B-mode ultrasound imaging guidance. For example, in imaging transducer element can be employed to provide a two-dimensional echocardiographic view of a diseased mitral valve (e.g., mitral annulus subjected to some degree of calcification) of a patient. For example, ultrasound imaging component 114 can be used to survey the mitral valve in order to identify the areas and the extent of mitral annular calcification and mitral leaflet calcification. Moreover, ultrasound imaging component 114 can also be configured to capture image data that assist with the visualization of mitral valvular leaflet excursion.

In addition, ultrasound imaging component 114 can be configured to utilize Doppler echocardiographic to evaluate the severity of the mitral dysfunction or calcification. More specifically, ultrasound imaging component 114 can be used to estimate the mean mitral pressure gradient, mitral annulus planar systolic excursion, the diastolic pressure half time, and an estimation of effective orifice area by the continuity equation (e.g., using left ventricular outflow tract flow) and the proximal isovelocities surface area method. Notably, mitral valve stenosis severity can be evaluated by different echocardiographic methods including planimetry, continuity equation, pressure half-time and by the proximal isovelocity surface method. In addition, ultrasound imaging component 114 can capture images that can be used by system controller engine 110 to estimate mitral valve regurgitation.

As indicated above, ultrasound imaging component 114 can be used to provide procedural guidance for TU applications by utilizing imaging ultrasound and electrocardiography. In some embodiments, foci of calcification and regional restrictions in leaflet mobility are used to identify targets of interest in the mitral valve. In addition, in-line electrocardiographic images captured by ultrasound imaging component 114 can be used for determination of cardiac phases with minimal annular motion or movement (e.g., typically during end-systole). These cardiac phases can be mapped as a percentage intervals of the interval period between two electrocardiographic R-waves. In some embodiments, system controller engine 110 can utilize the determined cardiac phases to select the timing of therapeutic ultrasound application (e.g., synchronized gated imaging).

In some embodiments, therapeutic ultrasound system 102 utilizes guidance from B-mode imaging of ultrasound imaging component 114 for proper positioning with respect to the patient's mitral valve. In particular, the therapeutic transducer elements of transducer array 112 are positioned using the B-mode guidance in such a manner that the therapeutic ultrasound device is able to align the focal zone and the depth with the mitral valve therapeutic target areas or ROI. After the physical positioning of the therapeutic transducer elements of the system 102 is achieved with respect to the heart and the chest wall of the patient target, therapeutic ultrasound system 102 may be configured to test each of the individual therapeutic transducer elements for excessive acoustic impedance caused by target shielding from internal body structures (e.g., ribs of patient). In some embodiments, individual therapeutic transducer elements can be singularly deactivated by system controller engine 110 if it is determined that said therapeutic elements are associated with high levels acoustic impedance. In such instances, system controller engine 110 and/or therapeutic controller 128 may be configured to deactivate the therapeutic transducer elements that are directed to these high impedance areas (i.e., in embodiments where the therapeutic beamformer is further configured to operate in a receive mode).

After the therapeutic ultrasound system 102 is properly positioned and the active therapeutic transducer elements are selected, an imaging transducer element in ultrasound imaging component 114 can be used for real-time confirmation of cavitation or mechanical disruption (e.g., the presence of white spots in the captured image) Notably, therapeutic ultrasound transducer array 112 can be activated and a real-time, high temporal resolution B-mode guidance ultrasound can be used to verify the presence and location of cavitation events (e.g., a cavitation cloud) at the focal zone (e.g., a therapeutic target). In some embodiments, the cavitation cloud is electronically steered to confirm the co-localization of the target area on the mitral valve using the imaging guidance provided by ultrasound imaging component 114. Afterwards, the therapeutic ultrasound transducer array can be configured to emit an HIFU pulse wave. Notably, therapeutic ultrasound system 102 is configured to coordinate real-time imaging that is used to verify the ongoing cavitation production in the mitral valve and thereby avoid cavitation cloud "drift" away from the target area. In addition, the real-time imaging conducted by the ultrasound imaging component 114 allows for monitoring of potential morphologic or function changes in the mitral valve and/or annulus. Further, the pulse wave emitted by therapeutic ultrasound device can be interrupted in the event of deteriorating leaflet coaptation, disruption of the mitral annulus, or the presence of intravascular calcific debris is detected. After it is determined that one therapeutic target subregion is satisfactorily treated, the focal zone of the therapeutic ultrasound device is then steered to the next target subregion of the mitral valve (e.g., a subsection of the mitral annulus). Notably, therapeutic ultrasound treatment pulse waves emitted by therapeutic ultrasound transducer array 112 proceeds to different mitral subregions in a sequential manner, under real-time imaging guidance afforded by the ultrasound imaging component to verify positioning and effect.

Once the entire target set of the mitral valve is treated, a complete echocardiographic (ECG) survey of the mitral valve is subsequently performed. Specifically, the ultrasound imaging component 114 can be used to determine the mitral valve structure and function. Quantification of mitral stenosis severity and regurgitation is similarly performed by the therapeutic ultrasound device. Changes in the mitral annular morphology, echogenicity, an annular excursion may also be documented. In the event of an incomplete therapeutic response by the mitral valve, therapeutic ultrasound system 102 can be used to repeat therapeutic treatment at selected subregions of the mitral valve. A final survey can be performed to establish post treatment mitral valve functionality.

In some embodiments, the therapeutic ultrasound device can be optimized to effect decalcification using various ultrasound parameters. For example, therapeutic ultrasound transducer array 112 can be configured to emit a pulse wave characterized by approximately 10 megapascals (MPa) of pressure in order to affect the calcification. In addition, therapeutic ultrasound transducer array 112 can be set to an operating frequency of approximately 1.0 MHz. Notably, the frequency is not important except to the extent that it controls focusing and losses due to frequency dependent attenuation. Lastly, the pulse repetition frequency can be set to 100 Hz for a duration of 10 or more minutes.

FIG. 2 is a schematic diagram of an exemplary dual function therapeutic ultrasound component device according to an embodiment of the subject matter described herein. In FIG. 2, dual function TU component 104 is depicted as including both a therapeutic ultrasound transducer array 112 (and shield covering) and an ultrasound imaging component 114. In this particular embodiment, therapeutic ultrasound transducer array 112 and ultrasound imaging component 114 are situated such that the ultrasound imaging component 114 is centrally positioned within therapeutic ultrasound transducer array 112. Therapeutic ultrasound transducer array 112 comprises 128 or 256 therapeutic transducer elements that can be arranged in an Archimedean spiral. In some embodiments, ultrasound imaging component 114 may be concentrically situated within the aperture of therapeutic ultrasound transducer array 112 in such a manner that the combination of therapeutic ultrasound functionality and real-time B-mode ultrasound for imaging guidance can be practically achieved.

Figure 3A:
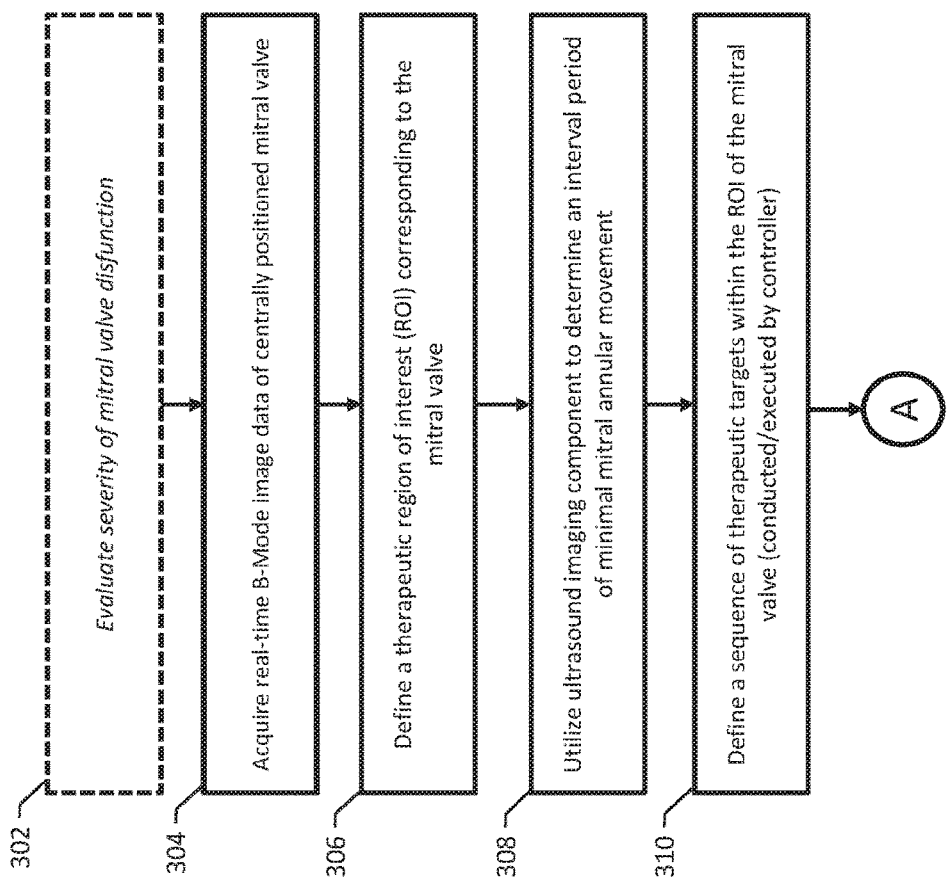
FIGS. 3A and 3B illustrate a flow diagram of an exemplary method for providing therapeutic ultrasound to a mitral valve according to an embodiment of the subject matter described herein.
Figure 3B:
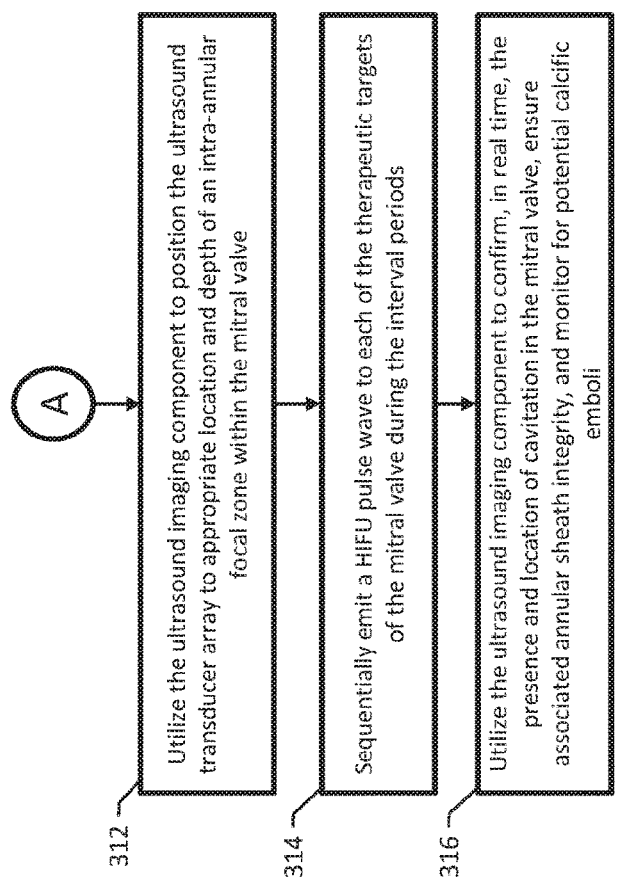

FIGS. 3A and 3B illustrate a flow diagram of an exemplary method 300 for providing therapeutic ultrasound to a mitral valve according to an embodiment of the subject matter described herein. In some embodiments, method 300 comprises a software algorithm or program (e.g., system controller engine) that is stored in memory and executed by a processor of the therapeutic ultrasound management device.

In block 302, the severity of the mitral valve dysfunction is evaluated. In some embodiments, the ultrasound imaging component can be used to capture images that provide a visual assessment of leaflet and annular mobility of a mitral valve. The system controller engine may also be configured to utilize the captured image data to estimate a mean diastolic pressure gradient across the mitral valve. Similarly, the system controller engine can be configured to estimate the mitral effective orifice area (e.g., using a continuity equation that use left ventricle outflow tract as a reference). Moreover, the controller engine can also be used to estimate the mitral effective orifice area by the proximal isovelocity surface area method. After making these estimations and measurements, the controller engine is configured to determine the presence and the severity of mitral annular calcification and/or mitral valve regurgitation in the patient subject.

In block 304, real-time B-mode image data of the mitral valve is acquired. In some embodiments, gated imaging of the mitral valve is conducted via the ultrasound imagining component. Specifically, the ultrasound imaging component can be used to conduct ECG gated imaging of a centrally positioned mitral valve annulus in real-time.

In block 306, a therapeutic region of interest (ROI) corresponding to the mitral valve is defined. In some embodiments, the system controller engine receives ROI selection input from an operator via a user interface. Notably, the selection input is derived from the captured image data obtained by the ultrasound imagining component and comprises one or more image blocks corresponding to mitral valve tissue that resides within the ROI and requires decalcification (e.g., removal of calcium within the annulus of the mitral valve). For example, a therapeutic region of interest can be defined using the ultrasound imaging component (e.g., in B-mode) to can back and forth over the mitral valve and identify the calcification present in the annulus. Calcification may appear on the display as white spots of isometric dimensions.

In block 308, an interval period of minimal mitral annular movement is identified. In some embodiments, the ultrasound imaging component captures images that the system controller engine is able to process and determine the time interval in which the mitral valve annulus exhibits minimum movement. The system controller engine is then able to measure and define this interval in terms of a percent of the R-R interval. Notably, the defined time interval corresponds to a particular phase of the cardiac cycle that involves minimal annular motion. In some embodiments, this interval may be determined by integration of B-mode and M-mode ultrasound and visualization of the mitral annulus conformation over time.

In block 310, a sequence of therapeutic targets within the ROI of the mitral valve is defined. In some embodiments, the system controller engine initially segments the defined ROI (established in block 306) into a number of therapeutic target segments that will be individually addressed by the TU system. The system controller engine subsequently defines a sequence in which the therapeutic targets are to receive a pulse wave from the therapeutic ultrasound transducer array. The defined sequence can be established based on the proximity and adjacency of the therapeutic targets with respect to each other. Further, the defined sequence defined by the system controller engine will attempt to avoid overlapping of the therapeutic targets.

In block 312, the ultrasound imaging component is utilized to position the therapeutic ultrasound transducer array. In some embodiments, the therapeutic transducer elements of the therapeutic ultrasound transducer array are positioned and guided by patient specific anatomy and the use of B-mode ultrasound guidance of the ultrasound imaging component to ensure appropriate location and depth of the therapeutic focal zone within the annulus of the mitral valve (e.g., a correct location and depth within the interior of the mitral annulus). Specifically, the therapeutic ultrasound transducer array is positioned such that the location and depth of the emitted pulse wave will be delivered to one of the defined therapeutic targets within the annulus of the mitral valve. Moreover, the therapeutic ultrasound transducer array is positioned in such a manner to avoid extra-annular calcium on the mitral valve.

In block 314, a HIFU pulse wave is emitted in sequence to each of the therapeutic targets of the mitral valve during the interval periods. In some embodiments, therapeutic ultrasound is applied by emitting pulsed cavitation treatment (i.e., a HIFU pulse wave) at the therapeutic target areas, such as those defined in blocks 306 and in accordance with the sequence defined in block 310. Further, the pulse wave is applied by the therapeutic ultrasound transducer array only during the segment of the R-R interval period that corresponds to the minimal annular movement as identified in block 308. Notably, the HIFU pulse wave is emitted to each of the therapeutic targets in sequence until the entire ROI (as defined in block 306) is treated.

In block 316, the ultrasound imaging component is utilized to confirm the presence and location of cavitation in the mitral valve. For example, real-time B-mode ultrasound guidance provided by the ultrasound imaging component is used to confirm in real-time the presence and appropriate location of cavitation in the mitral valve, to ensure that the annular sheath integrity is maintained, and to monitor for potential calcific emboli (i.e., extra-annular calcium that can inadvertently detach the annulus).

Once the therapeutic ultrasound therapy is applied in the manner described above with respect to FIGS. 3A and 3B, the efficacy of the therapy can be evaluated. In some embodiments, an evaluation of the severity of mitral valve dysfunction as described above in the description of block 302 can be repeated. Moreover, a survey may be performed for other changes, including annular disruption, release of calcium, and the development of new or worsening mitral valve regurgitation. After the aforementioned evaluation(s), the therapeutic ultrasound can be repeated as needed. For example, subregions of the mitral valve target with an incomplete response to initial treatment can be (re)treated. After this reapplication of therapeutic ultrasound (if necessary), a final evaluation of valve function is conducted. Similarly, the final evaluation is disclosed above in the description of block 302.

Figure 4:
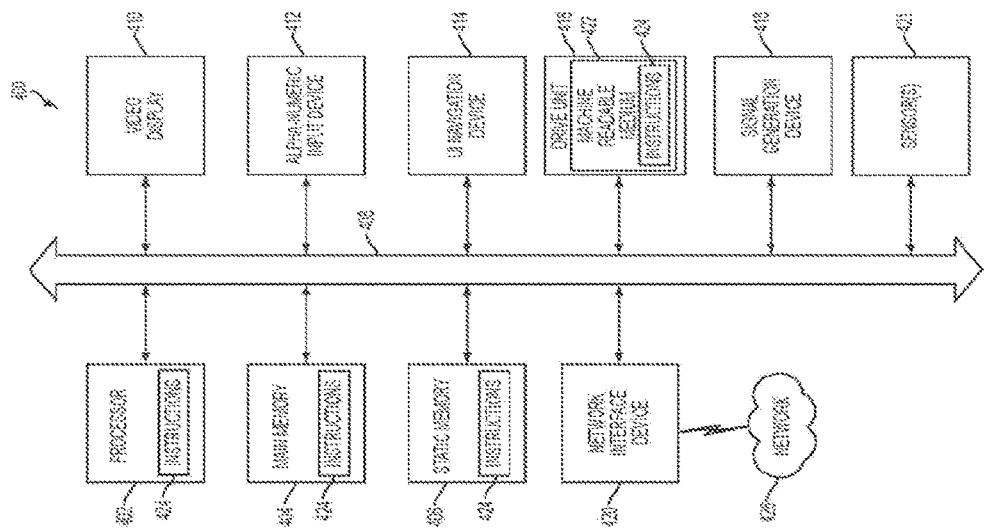
FIG. 4 is a block diagram of an exemplary therapeutic ultrasound control machine configured to execute the therapeutic ultrasound engine according to an embodiment of the subject matter described herein.

FIG. 4 is a block diagram illustrating an example of a TU control machine (such as TU control device 103 in FIG. 1) upon which one or more aspects of embodiments of the disclosed subject matter can be implemented. Examples of TU control machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application, such as a system controller engine) as a circuit that operates to perform certain operations as described herein. In an example, the software can reside on a non-transitory machine readable medium. In an example, the software (e.g., software based system controller engine), when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., Tu control machine 400) and software architectures that can be deployed in example embodiments.

In an example, TU control machine 400 can operate as a standalone device or the machine 400 can be connected (e.g., networked) to other machines.

In a networked deployment, the TU control machine 400 can operate in the capacity of either a server or a client machine in server-client network environments. In an example, TU control machine 400 can act as a peer machine in peer-to-peer (or other distributed) network environments. The TU control machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the TU control machine 400. Further, while only a single machine 400 is illustrated, the term "machine" shall also be taken to include any collection of machines that individually or jointly execute a set (or multiple sets) of instructions to perform any one or more of the methodologies discussed herein.

TU control machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 810, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or any other like sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine-readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks. The concept of applying a therapeutic ultrasound system and method for heart valve decalcification may be implemented and utilized with the related processors, networks, and computer systems.

It should be appreciated that any of the components, elements, engines, or modules referred to with regards to any of the presently disclosed embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

Some aspects of the present disclosure relate to magnetic resonance imaging (MRI) or ultrasound or other imaging modalities. Some disclosed embodiments relate to a system, method, and computer readable medium for applying ultrasound system and method for heart valve decalcification.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

It should be appreciated that as discussed herein, a subject or patient may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

Additional descriptions of aspects of the present disclosure will now be provided with reference to the accompanying drawings. The drawings form a part hereof and show, by way of illustration, specific embodiments or examples. In referring to the drawings, like numerals represent like elements throughout the several figures.

It should be appreciated that various sizes, dimensions, contours, rigidity, shapes, flexibility and materials of any of the components or portions of components in the various embodiments discussed throughout may be varied and utilized as desired or required.

In summary, while the disclosed subject matter has been described with respect to specific embodiments, many modifications, variations, alterations, substitutions, and equivalents will be apparent to those skilled in the art. The disclosed subject matter is not to be limited in scope by the specific embodiment described herein. Indeed, various modifications of the disclosed subject matter, in addition to those described herein, will be apparent to those of skill in the art from the foregoing description and accompanying drawings. Accordingly, the disclosed subject matter is to be considered as limited only by the spirit and scope of the disclosure including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A therapeutic ultrasound system comprising:
   a therapeutic ultrasound (TU) transducer array comprising a plurality of therapeutic transducer elements configured to generate a high-intensity focused ultrasound (HIFU) pulse wave that is directed to a mitral valve of a target patient;
   an ultrasound imaging component configured for capturing images corresponding to the mitral valve and for providing real-time steering guidance for the therapeutic ultrasound transducer array; and
   a system controller engine for determining an interval period of minimal annular movement exhibited by the mitral valve, coordinating an alternating operation of the ultrasound imaging component and the therapeutic ultrasound transducer array with respect to annular movement exhibited by the mitral valve, and coordinating emission of the high intensity focused ultrasound (HIFU) pulse wave by the therapeutic ultrasound transducer array to the mitral valve only during the determined interval period of minimal annular movement.

2. The therapeutic ultrasound system of claim 1, wherein the imaging component and the therapeutic ultrasound transducer array are synchronized by the system controller engine in such a manner that the ultrasound imaging component and the therapeutic ultrasound transducer array are prevented from operating simultaneously.

3. The therapeutic ultrasound system of claim 1, wherein the system controller engine is configured to determine cardiac phases associated with at least the annular movement exhibited by the mitral valve and to subsequently select a timing of TU application based on the determined cardiac phases.

4. The therapeutic ultrasound system of claim 1, wherein the therapeutic ultrasound transducer array is configured to be located external to the body of the target patient.

5. The therapeutic ultrasound system of claim 1, wherein the ultrasound imaging component is configured to generate two-dimensional echocardiographic views of the mitral valve.

6. The therapeutic ultrasound system of claim 1, wherein the ultrasound imaging component is configured to determine a foci of calcification within the mitral valve.

7. A method comprising:
   acquiring, via an ultrasound imaging component, imaging data of a mitral valve in real-time;
   defining a therapeutic region of interest corresponding to the mitral valve;
   utilizing, by a system controller engine, imaging data from the ultrasound imaging component to determine an interval period of minimal mitral annular movement;
   defining a sequence of therapeutic targets within the region of interest of the mitral valve;
   utilizing the imaging data acquired in real-time by the ultrasound imaging component to provide a therapeutic ultrasound transducer array with a location and depth of an intra-annular focal zone within the mitral valve; and
   emitting a high intensity focused ultrasound (HIFU) pulse wave from the therapeutic ultrasound transducer array to each of the therapeutic targets of the mitral valve only during the determined interval period of minimal mitral annular movement and in accordance with the defined sequence.

8. The method of claim 7, wherein the imaging component and the therapeutic ultrasound transducer array are synchronized by the system controller engine in such a manner that the ultrasound imaging component and the therapeutic ultrasound transducer array are prevented from operating simultaneously.

9. The method of claim 7, wherein the system controller engine is configured to determine cardiac phases associated with at least an annular movement exhibited by the mitral valve and to subsequently select a timing of a therapeutic ultrasound application based on the determined cardiac phases.

10. The method of claim 7, wherein the therapeutic ultrasound transducer array is configured to be located externally to a patient body.

11. The method of claim 7, wherein the ultrasound imaging component is configured to generate two-dimensional echocardiographic views of the mitral valve.

12. The method of claim 7, wherein the ultrasound imaging component is configured to determine a foci of calcification within an annular sheath of the mitral valve.

13. The method of claim 7 further comprising utilizing the ultrasound imaging component to identify regions of intra-annular and extra-annular calcification in the mitral valve.

14. The method of claim 7, wherein defining a sequence of therapeutic targets within the region of interest of the mitral valve further includes selecting intra-annular calcium foci as the therapeutic targets and avoiding extra-annular calcium.

15. The method of claim 7 further comprising utilizing the ultrasound imaging component to confirm a presence and location of cavitation in the mitral valve, maintain annular sheath integrity in the mitral valve, and monitor for potential calcific emboli.

16. A non-transitory computer readable medium having stored thereon executable instructions that when executed by a processor of a computer control the computer to perform steps comprising:
   acquiring, via an ultrasound imaging component, imaging data of a mitral valve in real-time;
   defining a therapeutic region of interest corresponding to the mitral valve;
   utilizing, by a system controller engine, imaging data from the ultrasound imaging component to determine an interval period of minimal mitral annular movement;
   defining a sequence of therapeutic targets within the region of interest of the mitral valve;
   utilizing the imaging data acquired in real-time by the ultrasound imaging component to provide a therapeutic ultrasound transducer array with a location and depth of an intra-annular focal zone within the mitral valve; and
   emitting a high intensity focused ultrasound (HIFU) pulse wave from the therapeutic ultrasound transducer array to each of the therapeutic targets of the mitral valve only during the determined interval period of minimal mitral annular movement and in accordance with the defined sequence.

17. The non-transitory computer readable medium of claim 16 further comprising utilizing the ultrasound imaging component to identify regions of intra-annular and extra-annular calcification in the mitral valve.

18. The non-transitory computer readable medium of claim 16, wherein defining a sequence of therapeutic targets within the region of interest of the mitral valve further includes selecting intra-annular calcium foci as the therapeutic targets and avoiding extra-annular calcium.

19. The non-transitory computer readable medium of claim 16 further comprising utilizing the ultrasound imaging component to confirm a presence and location of cavitation in the mitral valve, maintain annular sheath integrity in the mitral valve, and monitor for potential calcific emboli.

* * * * *